April 16, 1946. W. I. JOHNSTON Plant Pat. 680
ROSE PLANT
Filed April 5, 1945
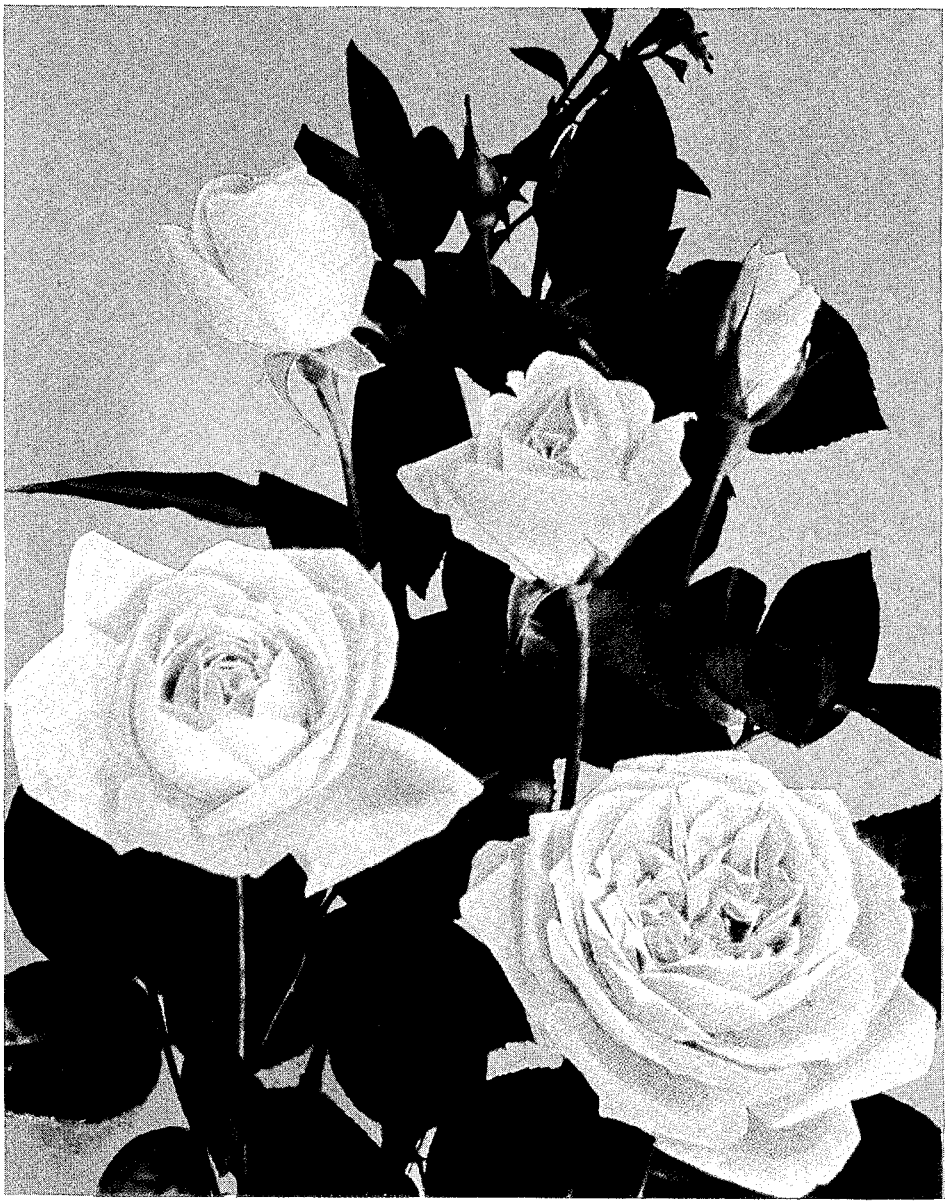
Inventor
W. I. Johnston
By Robb & Robb
His Attorneys Patented Apr. 16, 1946

Plant Pat. 680

UNITED STATES PATENT OFFICE

680

ROSE PLANT

Walter I. Johnston, Portadown, Ireland, assignor to Jackson & Perkins Company, Newark, N. Y., a corporation of New York Application April 5, 1945, Serial No. 586,681

1 Claim. (Cl. 47—61)

The present invention relates to a new and distinct variety of hybrid tea rose plant, the novelty of which resides primarily in the unique coloring of the flowers at the different stages of their development, combined with their Old Rose fragrance.

More specifically, as hereinafter pointed out and illustrated in the accompanying drawing, as nearly as possible to do so, the full-open flower is, generally speaking, a Light Fawn color, a characteristic absolutely new and different in the class of hybrid teas.

The color of the bud, dominantly Reed Yellow at the base and lighter toward the tip where it is overlaid with a light indication of Deep Purplish Vinaceous when the petals begin to unfurl, is also unique in the hybrid tea class. As the flower reaches the half-open stage, this coloring fades or changes, the center petals becoming Light Cinnamon Drab while the outer petals become a color combination of Pallid Quaker Drab as a base overlaid with Yellowish Glaucous.

The Old Rose fragrance in combination with the above mentioned color characteristics makes this new variety stand out as a most interesting and commercially valuable development from distinctly different seedling varieties.

Asexual reproduction shows that these characteristics hold true through succeeding propagations.

The following is a detailed description of this new variety, color terminology being in accord with Ridgway's Color Standard:

Parentage: Seedling.
*Seed Parent.*—Unnamed seedling.
*Pollen Parent.*—Unnamed seedling.
Classification: Botanic and commercial—hybrid tea.

*Flower*

(Observations made in the fields of Jackson & Perkins Company, Newark, New York, in the morning of August 15, 1944.)

Blooming habit: Recurrent—continuous.

Bud:

*Size.*—Medium.

*Form.*—Pointed; ovoid. Is not affected by wet weather but appears somewhat lighter in hot weather.

*Color.*—When sepals first divide—Chalcedony Yellow, Plate 17—lower half of petal. Upper half of petal, Eugenia Red, Plate 13. When petals begin to unfurl—Reed Yellow, Plate 30, which is dominant at the base and lighter towards tip where it is overlaid with a light indication of Deep Purplish Vinaceous, Plate 44. When half blown—inside of petals—center petals, Light Cinnamon Drab, Plate 46; outer petals, combination of Pallid Quaker Drab, Plate 51, as a base overlaid with Yellowish Glaucous, Plate 41; reverse of petals—Olive Buff, Plate 40, overlaid with Light Vinaceous Fawn, Plate 40.

*Sepals.*—Branched. Curl back when flowers begin to open. *Color*—Absinthe Green, Plate 31.

*Calyx.*—*Shape* — Oblong. *Size* — Long. *Aspect*—Smooth. *Color*—Light Cress Green, Plate 31.

*Peduncle.* — *Length* — Medium. *Aspect* — Prickly; very small prickles. *Color*—Light Cress Green, Plate 31, slight overcast of Hay's Russet, Plate 14. *Strength*—Stiff; erect.

*Opening.*—Opens up well. Is not affected by adverse conditions.

Bloom:

*Size.*—Large. Average size when fully expanded—4 inches to four and one-half inches.

*Borne.*—Singly and several together.

*Stems.*—Medium length; normal strength.

*Form.*—When first open—High center. *Permanence*—retains its form to the end.

*Petalage.*—Double (full but open center). Number of petals under normal conditions—40.

*Color.*—Center of flower—Light Vinaceous Fawn, Plate 40, lightly overcast with Mauvette, Plate 25. Outer petals—Light Mineral Gray, Plate 47, overlaid with Light Pinkish Lilac, Plate 37. Base of petals (aiglet)—Citron Yellow, Plate 16. Inside of petals—Light Vinaceous Fawn, Plate 40, lightly overcast with Mauvette, Plate 25. Reverse of petals—Pale Olive Buff, Plate 40. *General tonality from a distance.*—Light Vinaceous Fawn, Plate 40.

*Discoloration.*—General tonality at end of first day—Light Vinaceous Fawn, Plate 40. Second day—Light Vinaceous Fawn, Plate 40, overcast with Pale Olive Buff, Plate 40. Third day—Pale Vinaceous Fawn, Plate 40.

Petals:

*Texture.*—Thick. Is not affected by wet or hot weather.

*Appearance.* — Inside — Shiny. Outside—Satiny.

*Form.*—Oval.

*Arrangement.*—Imbricated (regularly arranged shinglelike). Petaloids in center—few; small.
*Persistence.*—Drop off cleanly.
*Fragrance.*—Moderate. Nature—"Old Rose Perfume."
*Lasting quality.*—On the plant and as cut flower—Long.
Genitals organs:
*Stamens, Anthers*:
*Size.*—Medium.
*Color.*—Primuline Yellow, Plate 16.
*Arrangement.*—Regular around styles.
*Stamens, Filaments (threads)*:
*Length.*—Medium.
*Color.*—Carnelian Red, Plate 14.
*Pollen.*—Mustard Yellow, Plate 16.
*Styles.* — Bunched; short; thin; uneven length.
*Stigmas.*—Maize Yellow, Plate 4.
*Ovaries.*—All enclosed in calyx.

*Plant*

Form: Bush.
Growth: Vigorous; branching.
Foliage: 5–7 leaflets.
*Size.*—Medium.
*Quantity.*—Normal.
*Color.*—*New foliage:* upper side—Victoria Lake, Plate 1, with Oil Green, Plate 5, midrib; under side—Victoria Lake, Plate 1. *Old foliage:* upper side—Cress Green, Plate 31; under side—Light Cress Green, Plate 31.
*Shape.*—Oval pointed.
*Texture.*—Upper side—leathery; glossy; under side—rough.
*Ribs and veins.*—Ordinary.
*Edge.*—Serrated (saw toothed).
*Serration.*—Single; small.
*Leaf stem.*—Absinthe Green, Plate 31. Under side—Smooth.
*Stipules.*—Medium length; slightly bearded.
*Disease resistance.*—Resistant.
Wood:
*New wood.*—Maroon, Plate 1. *Bark*—smooth.
*Old wood.*—Cress Green, Plate 31. *Bark*—smooth.
Thorns:
*Thorns.*—*Quantity*—On main stalks from base and on laters from stalk—ordinary. *Form*—Broad base; medium length; straight. *Color when young*—Oxblood Red, Plate 1. *Position*—irregular.
*Prickles.*—*Quantity*—On main stalks and on laterals—few. *Color*—Pale Glass Green, Plate 31.
*Short needles.*—On main stalks and on laterals—none.

I claim:

A new and distinct variety of hybrid tea rose plant, characterized as to novelty by the unique coloring of the flowers in the different stages of their development, combined with their Old Rose fragrance, substantially as shown and described.

WALTER I. JOHNSTON.